(12) United States Patent
Luthra et al.

(10) Patent No.: US 6,287,707 B1
(45) Date of Patent: Sep. 11, 2001

(54) BIOCOMPATIBLE LUBRICIOUS HYDROPHILIC MATERIALS FOR MEDICAL DEVICES

(76) Inventors: Ajay Kumar Luthra, 219 Somervell Road, South Harrow, Middlesex HA2 8UA (GB); Shivpal Singh Sandhu, 63 Lascelles Road, Slough, Berkshire SL3 7PW (GB)

( * ) Notice: Subject to any disclaimer, the term of this patent is extended or adjusted under 35 U.S.C. 154(b) by 0 days.

(21) Appl. No.: 09/051,674

(22) PCT Filed: Oct. 17, 1996

(86) PCT No.: PCT/GB96/02557

§ 371 Date: Jun. 26, 1998

§ 102(e) Date: Jun. 26, 1998

(87) PCT Pub. No.: WO97/14448

PCT Pub. Date: Apr. 24, 1997

(30) Foreign Application Priority Data

Oct. 17, 1995 (GB) .................................................. 9521253

(51) Int. Cl.[7] ........................... B32B 27/30; C08F 265/04; C08F 8/14
(52) U.S. Cl. ........................ 428/522; 525/303; 525/330.1; 525/330.6; 526/320
(58) Field of Search .................... 428/413, 480, 428/522; 526/320; 525/330.1, 330.6, 303

(56) References Cited

U.S. PATENT DOCUMENTS

| | | |
|---|---|---|
| 3,933,943 * | 1/1976 | Fahrbach ............................. 260/887 |
| 4,200,563 | 4/1980 | Komiya . |
| 4,424,311 | 1/1984 | Nagaoka et al. . |
| 4,429,097 | 1/1984 | Chang et al. . |
| 4,728,696 | 3/1988 | Van Phung et al. . |
| 4,978,777 * | 12/1990 | Takagawa ............................. 560/224 |
| 5,075,400 | 12/1991 | Andrade et al. . |
| 5,480,953 * | 1/1996 | Sugaya et al. ....................... 526/320 |
| 5,731,387 * | 3/1998 | Zajaczkowski ................... 525/330.2 |

FOREIGN PATENT DOCUMENTS

| | | |
|---|---|---|
| 0 538 640 A1 | 4/1993 | (EP) . |
| 848919 | 9/1990 | (GB) . |
| WO 86/02087 | 4/1986 | (WO) . |

* cited by examiner

*Primary Examiner*—Paul Thibodeau
*Assistant Examiner*—Kevin R. Kruer
(74) *Attorney, Agent, or Firm*—Howell & Haferkamp, LC

(57) ABSTRACT

A biocompatible, lubricious, hydrophilic material useful for coating medical devices or for blending into polymer compositions intended for making medical devices comprises a terpolymer of 5 to 25 mole percent of a polymerisable monomer (1) having a polyethylene oxide unit with an average degree of polymerisation from 5 to 18 and a polymerisable carbon-carbon double bond, 5 to 30 mole percent of a polymerisable monomer (2) having a polyethylene oxide unit with an average degree of polymerisation from 19 to 65 and polymerisable carbon-carbon double bond, and 45 to 90 mole percent of an alkyl methacrylate (3): (1) $CH_2=C(R)-CO-[-O-CH_2-CH_2-]_{n1}-O-R$ where n1 is from 5 to 18, and each R is independently H or $CH_3$; (2) $CH_2=C(R)-CO-[-O-CH_2-CH_2-]_{n2}-O-R$ where n2 is from 19 to 65 and each R is independently H or $CH_3$; (3) $CH_2=C(CH_3)-CO_2-(CH_2)_m-CH_3$ where m is from 3 to 17, which may be made by the aqueous emulsion polymerisation of the monomers.

13 Claims, No Drawings

BIOCOMPATIBLE LUBRICIOUS HYDROPHILIC MATERIALS FOR MEDICAL DEVICES

CROSS-REFERENCE TO RELATED APPLICATIONS

This is a 35 U.S.C. 371 national stage application of International Application No. PCT/GB96/02557, filed Oct. 17, 1996, which claims priority from GB Application No. 9521253.6, filed Oct. 17, 1995.

BACKGROUND OF THE INVENTION

In recent years there has been an increased awareness of the need for biocompatible materials for medical devices. Currently medical devices are typically made from synthetic polymeric materials such as polyvinylchloride (PVC), polyurethanes (PU), polybutadienes (latex), polyamides (PA) and others. It has also been recognized that hydrophilic materials offer good biocompatibility to medical devices when in-contact with biological fluids or living tissue. These hydrophilic materials significantly reduce adsorption of proteins and of cellular components such as platelets, leucocytes, erythrocytes and fibroblasts, and also reduce activation of intrinsic and extrinsic blood clotting pathways.

In addition to the biocompatibility of the material, the lubricity of the coating is also important, as it minimises patient trauma, and allows ease of insertion and removal of the device. An example of an important application of a biocompatible lubricious hydrophilic material is during chest drainage, which occurs after cardio-thoracic surgery. In this chest drainage procedure, preformed blood clots and whole blood is able to slide down the medical device such as thoracic drain catheter. This is achieved because of the lubricious (slippery) nature of the coated device. A biocompatible lubricious hydrophilic medical device can be used in other wound drain applications.

It has been well recognized that polyethylene oxide (PEO) (also called polyethylene glycol or PEG) when bound to a medical device offers good biocompatibility, lubricity and hydrophilicity. U.S. Pat. No. 4,424,311 discloses a polymerizable PEO monomer having polyethylene oxide unit with a carbon-carbon double bond which is grafted on to PVC or vinyl chloride-vinyl acetate copolymer or vinyl chloride-vinyl acetate-ethylene terpolymer. Disadvantages of grafting PEO are that it is a lengthy procedure and the grafted PEO units are unevenly distributed. Therefore, homogenous coverage on the surface is not achieved, which results in reduced biocompatibility and lubricity.

In another U.S. Pat. No. 5,075,400, PEO containing a polymerizable carbon-carbon double bond is polymerised, in toluene, with methyl methacrylate or ethyl methacrylate. The resultant polymer, which is referred to as supersurfactant, is predominantly water soluble and is adsorbed onto various polymeric surfaces from water, water/ethanol mixtures, or ethanol. A disadvantage of these polymers is that they act as surfactants, are adsorbed on to the surface and therefore would be readily de-sorbed from the surface when they are in contact with biological fluids such as blood, as blood has surfactant properties. Similarly, the lubricious properties would also be lost since the adsorbed surfactant is not stable on the surface. Another disadvantage is that the polymer supersurfactant is synthesized by solution polymerization in toluene and as a result high molecular weight polymer containing PEO would be difficult to produce, since PEO polymers have limited solubility in toluene.

BRIEF SUMMARY OF THE INVENTION

It is an object of the present invention to mitigate or overcome some of the aforementioned disadvantages encountered in the prior art.

The present invention is concerned with biocompatible, lubricious, hydrophilic materials suitable for use in medical devices or otherwise. It is proposed that the materials may be used to coat a substrate such as a medical device or may be blended into a polymer composition prior to formation of the medical device or other article. The invention extends to polymers, their production methods, and their uses as coatings or components of articles of manufacture.

In one aspect of the present invention a biocompatible, lubricious, hydrophilic material for medical devices or other applications can be produced by aqueous emulsion polymerization to yield a polymer with the desired hydrophobic and hydrophilic domains, not conventionally obtained by solution polymerization, wherein the emulsion polymer produced is a stable emulsion having high molecular weight.

DETAILED DESCRIPTION OF THE INVENTION

In accordance with a more specific aspect of the invention, there is provided a biocompatible, lubricious, hydrophilic material comprising a terpolymer of 5 to 25 mole percent of a polymerizable monomer (1) having a polyethylene oxide unit with an average degree of polymerization from 5 to 18 and a polymerizable carbon-carbon double bond, 5 to 30 mole percent of a polymerizable monomer (2) having a polyethylene oxide unit with an average degree of polymerization from 19 to 65 and polymerizable carbon-carbon double bond, and 45 to 90 mole percent of an alkyl methacrylate (3):

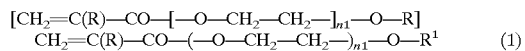  (1)

where n1 is from 5 to 18, and [each] R and $R^1$ are [is] independently H or $CH_3$

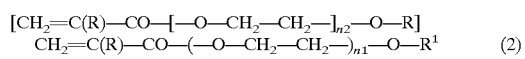  (2)

where n2 is from 19 to 65, and [each] R and $R^1$ are [is] independently H or $CH_3$

  (3)

where m is from 3 to 17.

Monomers (1) and (2) are hydroxy or, preferably, methoxy polyethyleneglycol acrylates or, preferably, methacrylates, and provide the hydrophilic moieties in the terpolymer. Monomer (3), ranging from butyl to octadecyl methacrylate, provides the hydrophobic moieties.

The preferred molar proportions of (1), (2) and (3) are about 15% each of (1) and (2) and 70% of (3). In weight terms, proportions of 6 to 20% of (1), 40 to 80% of (2) and 10 to 50% of (3) are generally appropriate.

It is preferred that monomer (1) has polyethylene oxide units with a degree of polymerization n1 from 5 to 12, more especially a degree of polymerization n1 from 5 to 10.

It is preferred that monomer (2) has polyethylene oxide units with a degree of polymerization n2 from 20 to 50, more especially a degree of polymerization n2 from 22 to 48.

It is preferred that monomer (3) is n-butyl methacrylate.

The incorporation of significant proportions of monomer (2) of higher molecular weight than monomer (1) allows the formation of a solid dry powdery product with advantageous properties of handling, processing and storage.

The production of a terpolymer by polymerizing monomers (1), (2) and (3) may be carried out in water to produce an aqueous emulsion polymer which is stable, having high molecular weight.

The production of the terpolymer in water differs significantly from production in organic solvents in two respects.

a) Higher molecular weights of the terpolymer can be achieved by emulsion polymerisation than by solution polymerisation in organic solvents, as PEO solubility decreases with increasing molecular weight for polymerisation carried out in organic solvents such as toluene, ethyl and butyl acetate, alcohols etc.

b) Aqueous emulsion polymerisation allows polymers to be produced where the hydrophobic monomer (3) is phase separated to a certain degree to produce a polymer having hydrophilic and hydrophobic domains. This allows the polymer to be adsorbed, solvent welded or blended with PVC, polyurethanes, polybutadienes and the like. Polymerisation of the above three monomers (1), (2) and (3) in organic solvents produces polymers which are random, and phase separated domains of hydrophilic and hydrophobic do not occur. This results in poor adhesion of the polymer on to PVC, polyurethanes, polybutadienes and the like.

Aqueous emulsion polymerisation of monomers (1), (2) and (3) can be initiated by conventional water soluble initiators such as potassium persulphate. After polymerisation, the terpolymer is dialyzed against water to remove unreacted monomer and the resultant polymer is freeze dried, spray dried or treated by other means to obtain a dry powder.

The resultant terpolymer may then be dissolved in organic solvents, such as alcohols, acetone or tetrahydrofuran (THF) or mixtures thereof, and coated on to prefabricated devices, or blended with other polymers, such as PVC, polyurethanes, polybutadienes and the like.

The coating of the terpolymer on to medical devices made from PVC, PVC blended with other polymers such as polyurethanes, vinyl chloride-vinyl acetate copolymer or vinyl chloride-vinylacetate-ethylene terpolymer, PU, PA and the like can be carried out by dripping, spraying or any other means by which a homogenous coating may be obtained on the substrate, followed by any necessary drying out.

Depending on the choice of the solvent and substrate the coating can be adsorbed onto the surface or it can be solvent welded. For instance, if the coating is dissolved in a solvent such as THF and the substrate to be coated is polyethylene (PE), only an adsorbed coating will be produced, since THF is a non-solvent for PE. If however the substrate is PVC the coating can be classified as being solvent welded, since THF is a known solvent for PVC. The terpolymer penetrates deep into the PVC polymer, thereby producing a very durable biocompatible, lubricious, hydrophilic coating on the PVC substrate.

As for polybutadiene (latex rubber), the terpolymer can be coated onto a preformed device from a suitable organic solvent; or the emulsion polymer, after dialysis, can be added directly to and blended with the latex and a medical device can then be fabricated from the mixture.

Similarly, for treating polyurethanes, the terpolymer can be coated onto a preformed device from a suitable solvent or it can be melt-mixed with the polyurethane and then the device fabricated.

EXAMPLE 1

Methoxy polyethyleneglycol methacrylates (monomers (1) and (2), R being methyl throughout) were purchased from International Speciality Chemicals, UK. Butyl methacrylate (monomer (3), m being 3) and potassium persulphate were purchased from Aldrich Chemical Co., UK. 192 g Methoxy polyethyleneglycol methacrylate with molecular weight of 2000 and with a polyethylene oxide unit number $n2$ of approximately 45 (0.1 mole) (MPEG2000MA) was added to 100 ml of water. On dissolving the MPEG2000MA, 36 g of methoxy polyethyleneglycol methacrylate with a molecular weight of 350 and with a polyethylene oxide unit number $n1$ of approximately 8 (0.1 mole) (MPEG350MA) was added, together with 72 g of n-butyl methacrylate (0.46 mole). The molar proportions of MPEG350MA (1): MPEG2000MA (2): n-butyl methacrylate (3) were accordingly 15:15:70.

A 2 litre three-necked round bottom flask fitted with a reflux condenser, a thermometer and a nitrogen bleed was charged with 1180 ml of distilled water and heated to 80° C. The monomer solution was poured into the reaction vessel and polymerization was initiated with the addition of 2 g of potassium persulphate. The reaction was allowed to proceed for 10 minutes and then the reaction vessel was cooled to room temperature. A milky white viscous aqueous emulsion polymer resulted. The polymer was dialyzed against water for 24 to 48 hours. The dialyzed polymer was then freeze dried to obtain a white powder with a yield of 80%.

Aqueous based Gel Permeation Chromatography (GPC) was conducted on the aqueous emulsion after dialysis. The emulsion polymer had a molecular weight distribution in the range 40–70 kilodaltons.

Other monomer concentrations within the embodiments of this invention were also used to synthesize the aqueous polymer emulsions. All polymers synthesized gave molecular weight distributions in the range 40–70 kilodaltons.

EXAMPLE 2

Adsorption and solvent welding of terpolymer on to hydrophobic surfaces.

a) Adsorption

Test pieces of low density polyethylene (PE) sheets were cut in 2 $cm^2$ pieces and then dipped into a THF solution containing 1.5% w/v of the terpolymer produced in Example 1. The PE sheets were allowed to dry at room temperature for 24 hours.

b) Solvent Welding

Thoracic drain catheters (supplied by Portex Ltd, UK) made from plasticized PVC were dipped into a THF solution containing 1.5% w/v of the terpolymer produced in Example 1 and allowed to dry at room temperature for 24 hours.

EXAMPLE 3

PE sheets and PVC tubing coated as in Example 2 were then assessed for platelet adhesion using whole blood from volunteers. Platelet adhesion on coated and uncoated test samples was measured using standard ATP luminescence technique.

Table 1 shows the results of platelet adhesion studies. The results clearly show that there is a dramatic reduction in platelet adhesion on coated samples relative to the uncoated. There is a greater than 90% reduction in platelet adhesion on coated samples.

TABLE 1

Platelet Adhesion (platelets × 10⁶)

| | Volunteer Number | | | | |
|---|---|---|---|---|---|
| | 1 | 2 | 3 | 4 | Mean |
| Uncoated PE | 78.08 | 90.67 | 97.54 | 104.08 | 72.19 |
| Coated PE | 4.32 | 6.45 | 5.88 | 5.89 | 5.635 |
| Uncoated PVC tubing | 54.02 | 73.36 | 69.31 | 108.04 | 76.18 |
| Coated PVC tubing | 4.21 | 4.77 | 5.74 | 3.08 | 4.45 |

EXAMPLE 4

PVC tubing was coated with the terpolymer as described in Example 2 and then tested for whole blood clotting times using Modified Lee White Test.

Approximately 10 mls of blood was withdrawn by clean venepuncture from healthy human volunteers. A known volume of blood was transferred into the PVC tubing which was clamped at one end. At approximately 15 second intervals the tubes were removed from a water bath (bath temperature –37° C.) and examined for any clot formation. Time taken for the blood to clot was recorded to the nearest quarter of a minute.

Table 2 shows the results of the above experiment. The results clearly show that the clotting time for the coated samples was double that of the uncoated samples.

TABLE 2

Modified Lee White Test (Time: minutes)

| | Volunteer Number | | | |
|---|---|---|---|---|
| | 1 | 2 | 3 | 4 |
| Uncoated PVC tubing | 5.25 | 5.50 | 5.25 | 5.33 |
| Coated PVC tubing | 11.00 | 10.5 | 11.00 | 10.83 |

What is claimed is:

1. A biocompatible lubricious, hydrophilic material which comprises a terpolymer of from 5 to 25 mole percent of a first monomer (1) having the formula $$CH_2=C(R)-CO-(-O-CH_2-CH_2-)_{n1}-O-R^1$$

wherein R and R¹ are independently H or CH₃ and $n_1$ is from 5 to 18; from 5 to 30 mole percent of a second monomer (2) having the formula $$CH_2=C(R)-CO-(-O-CH_2-CH_2-)_{n2}-O-R^1$$

wherein R and R¹ are independently H or CH₃ and $n_2$ is from 19 to 65; and from 45 to 90 mole percent of an alkyl methacrylate (3) having the formula $$CH_2=C(CH_3)-CO_2-(CH_2)_m-CH_3$$

wherein m is from 3 to 17.

2. A terpolymer according to claim 1 wherein R¹ in the first and R³ in the second monomers are each CH₃.

3. A terpolymer according to claim 1 which comprises 6 to 20% by weight of the first monomer (1), from 40 to 80% by weight of the second monomer (2), and from 10 to 50% by weight of the alkyl methacrylate (3).

4. A terpolymer according to claim 1 wherein $n_1$ is from 5 to 10.

5. A terpolymer according to claim 1 wherein $n_2$ is from 22 to 48.

6. A terpolymer according to claim 1 wherein the alkyl methacrylate is butyl methacrylate.

7. A terpolymer according to claim 1 which is a block copolymer with hydrophobic and hydrophilic domains.

8. A method of producing a terpolymer according to claim 7 which comprises subjecting the first monomer (1), the second monomer (2) and the alkyl methacrylate (3) to aqueous emulsion polymerization, dialyzing the resulting polymer against water to remove unreacted monomer, and drying the dialyzed terpolymer.

9. An article of manufacture having a lubricious biocompatible surface wherein said surface is provided by coating the article with a solution of a terpolymer according to claim 1.

10. An article of manufacture according to claim 9 wherein said article is a medical device.

11. A biocompatible lubricious hydrophilic material according to claim 1, comprising a blend of the terpolymer with at least one other polymer.

12. A medical device formed from a polymer composition according to claim 11.

13. A biocompatible lubricious hydrophilic material according to claim 11, wherein the at least one other polymer is selected from the group consisting of PVC, polyurethane, polybutadiene, and combinations thereof.

* * * * *